United States Patent
Yan et al.

(10) Patent No.: US 11,571,235 B2
(45) Date of Patent: Feb. 7, 2023

(54) ULTRASONIC SURGICAL BLADE, WAVEGUIDE AND ULTRASONIC SCALPEL THEREOF

(71) Applicant: INNOLCON MEDICAL TECHNOLOGY (SUZHOU) CO., LTD., Suzhou (CN)

(72) Inventors: Zhongyu Yan, Irvine, CA (US); Lei Wang, Suzhou (CN); Wei Luo, Suzhou (CN)

(73) Assignee: INNOLCON MEDICAL TECHNOLOGY (SUZHOU) CO., LTD., Suzhou (CN)

( * ) Notice: Subject to any disclaimer, the term of this patent is extended or adjusted under 35 U.S.C. 154(b) by 187 days.

(21) Appl. No.: 16/649,495

(22) PCT Filed: Jul. 2, 2018

(86) PCT No.: PCT/CN2018/093990
§ 371 (c)(1),
(2) Date: Mar. 20, 2020

(87) PCT Pub. No.: WO2019/076086
PCT Pub. Date: Apr. 25, 2019

(65) Prior Publication Data
US 2020/0305922 A1    Oct. 1, 2020

(30) Foreign Application Priority Data

Oct. 19, 2017   (CN) .......................... 201710980445.4

(51) Int. Cl.
*A61B 17/32*   (2006.01)
*A61B 17/3211*   (2006.01)

(52) U.S. Cl.
CPC .. *A61B 17/320068* (2013.01); *A61B 17/3211* (2013.01); *A61B 2017/320075* (2017.08); *A61B 2017/320082* (2017.08)

(58) Field of Classification Search
CPC ........ A61B 17/320068; A61B 17/3211; A61B 2017/320075; A61B 2017/320082; A61B 2017/320074; A61B 2017/320077
See application file for complete search history.

(56) References Cited

U.S. PATENT DOCUMENTS 4,128,351 A   12/1978   Kurtz et al.
8,348,880 B2   1/2013   Messerly et al.
(Continued)

FOREIGN PATENT DOCUMENTS

CN   1694649 A   11/2005
CN   201260686 Y   6/2009
(Continued)

*Primary Examiner* — Kathleen S Holwerda
*Assistant Examiner* — Lauren Dubose
(74) *Attorney, Agent, or Firm* — Seed Intellectual Property Law Group LLP (57) ABSTRACT

An ultrasonic surgical blade, wherein the blade has a curved shape, and both sides of the blade are provided with cutting surfaces, one surface is a concave surface and the other surface is a convex surface. The thickness of the blade is gradually thinned along a cutting direction from a proximal end to a distal end. The concave surface length is set as L1, the radius of curvature R1; the length of the convex surface L2, the radius of curvature R2; the angle of the bending of the center line of the blade is α; the diameter of the proximal end of the blade is D; the thickness of the most distal end surface of the blade is T. The relationship among them is: L1=L2+L2/1.5*(D−T)*SIN(α) (1), R1=R2+2T (2). The range of each size is adjustable within 10%. An ultrasonic wave guide and an ultrasonic scalpel using this blade have (Continued)

fewer potential resonant frequencies, so the thermal damage to the tissue is small, and the performance is more stable.

8 Claims, 5 Drawing Sheets

(56) References Cited

U.S. PATENT DOCUMENTS

| | | | | |
|---|---|---|---|---|
| 8,348,967 | B2 * | 1/2013 | Stulen | A61B 17/320068 |
| | | | | 606/169 |
| 9,358,030 | B2 | 6/2016 | Young et al. | |
| 11,058,449 | B2 * | 7/2021 | Beaupre | A61B 17/320092 |
| 2007/0191713 | A1 * | 8/2007 | Eichmann | A61B 17/1606 |
| | | | | 600/471 |
| 2010/0057118 | A1 | 3/2010 | Dietz et al. | |
| 2013/0116717 | A1 * | 5/2013 | Balek | A61B 17/320068 |
| | | | | 606/169 |
| 2013/0289592 | A1 | 10/2013 | Stulen et al. | |
| 2014/0005701 | A1 * | 1/2014 | Olson | A61B 17/320092 |
| | | | | 606/169 |
| 2016/0367281 | A1 * | 12/2016 | Gee | A61B 17/320092 |

FOREIGN PATENT DOCUMENTS

| | | | |
|---|---|---|---|
| CN | 101516276 | A | 8/2009 |
| CN | 102143715 | A | 8/2011 |
| CN | 106691544 | A | 5/2017 |
| CN | 106890020 | A | 6/2017 |
| EP | 1 138 264 | A1 | 10/2001 |
| EP | 3207886 | A1 | 8/2017 |
| WO | 2017/027745 | A1 | 2/2017 |

* cited by examiner

ULTRASONIC SURGICAL BLADE, WAVEGUIDE AND ULTRASONIC SCALPEL THEREOF

BACKGROUND

Technical Field

This invention relates to the field of medical devices, specifically ultrasonic blade, waveguide and ultrasonic scalpel.

Description of the Related Art

Ultrasonic scalpel large-scale applications have had more than 20 years of history. Comparing to other surgical methods, ultrasonic scalpel has advantages of producing less smoke, clearer surgical view field, smaller thermal damage; it combines multiple functions of tissue cutting, coagulation and dissection in one instrument, and is able to precisely control the cutting and coagulation area; no electrical damage; rapid ultrasonic oscillation has a self-cleaning effect, which reduces the sticking of blade with tissues.

Ultrasonic scalpel can be used for laparoscopic and endoscopic surgery, and for open surgery as well; can be used in combination with other surgical instruments, such as traditional mechanical scalpels and electrical knives, and can be used alone as well, because it combines multifunction of grasping, cutting, dissection and coagulation in one instrument. For different operations, suitable tool lengths are required in order to reach the surgical sites; and suitable hand piece and tool combination is required for easy operation.

Ultrasonic scalpel is a type of elongated ultrasonic vibration system. In the course of operation there may be potential resonant frequencies excited besides the main working resonant frequency. If this is the case, then the system will become unstable and unable to work. Some factors, such as the length of the ultrasonic wave guide, the lateral vibration mode of its body and the coupling state of the system, may affect the potential resonance. A small change may cause the potential resonance be excited, affecting the stability of the system.

If the ultrasonic scalpel has a large lateral vibration in the surrounding tissue which is not in the cutting direction, it may increase the area of lateral thermal damage. Especially for curved blade, this damage increases if the lateral vibrations were not suppressed well or other potential resonances were not well inhibited.

BRIEF SUMMARY

Provided is an ultrasonic blade, waveguide and ultrasonic scalpel thereof with reduced potential resonance and less tissue damage.

In order to solve technical issues, provided is an ultrasonic surgical blade; the blade is curved, and both sides of the blade are provided with cutting surfaces, one surface is concave and the other surface is convex. The thickness of the blade is gradually thinning along the cutting direction from the proximal end to the distal end. The concave length is L1, curvature radius is R1; the convex length is L2, curvature radius is R2; the bent angle of the blade center line is α; the proximal end diameter of the blade is D; the thickness of the blade distal end is T. They satisfy the following formula:

$$L1 = L2 + \frac{L2}{1.5} \times (D - T) \times Sin\alpha \quad (1)$$

$$R1 = R2 + 2T \quad (2)$$

The values of L1 and R1 are calculated by formulas (1) and (2), and the range of each value is ±10%.

An ultrasonic surgical waveguide, comprises the blade as described above. The proximate portion of the waveguide has two steps. The proximate end diameter is D1, the second proximate diameter distal to the first proximal step is D2, and the third proximate diameter distal to the second proximal step is D3; the ratio between each other is:

$$D3:D2:D1=(0.679\sim0.721):(0.7519\sim0.7081):(0.97\sim1.03)$$

Preferably, the waveguide also has a number of thinner sections, the diameter of the thinner section is D4, the diameter of the area between the thinner sections is same as the third proximate diameter D3; the ratio between each other is $$D4:D3=(0.8827\sim0.9373):(0.97\sim1.03)$$

In order to solve the above technical issue, the present invention provides an ultrasonic scalpel, comprises: the hand piece, the waveguide and the blade connected in sequence; the waveguide is as described above.

In order to solve the above technical issue, the present invention provides an ultrasonic surgical blade; it has the cutting surfaces on both the upper and lower sides of the blade; relative to the upper and lower sides, the left side or the right side of the blade has a gradually narrowed cutting toward the distal end of the blade; the proximate end of the blade is equipped with an arc-shaped groove; the groove is within ¼ wavelength from the distal end, and it is at the same side with the gradually narrowed cutting.

An ultrasonic surgical waveguide, comprises the blade as described above. The proximate portion of the waveguide has two steps. The proximate end diameter is D21, the second proximate diameter distal to the first proximal step is D22, and the third proximate diameter distal to the second proximal step is D23; the ratio between each other is:

$$D23:D22:D21=(0.6014\sim0.6386):(0.7004\sim0.6596):(0.97\sim1.03)$$

An ultrasonic scalpel, comprises: the hand piece, the waveguide and the blade connected in sequence; the waveguide is the one described above.

Through the relationship among the variables proposed above and the characteristics of the design, the present invention provides the structure and method of maintaining the pure longitudinal vibration of the waveguide, reducing the potential other resonant frequencies, reducing the lateral vibration of the blade, thereby reducing the thermal damage to the tissue body and increasing the stability of the system. As a slender ultrasonic surgical waveguide plus an blade with an asymmetric cutting shape, as described in this invention of the curved blade, one-sided cutting, if these cutting variables were not constrained and not to add other feature shapes, the blade will generate severely lateral vibration, and the waveguide will also produce lateral vibration. Severe lateral vibration of the blade can cause tissue damage, the lateral vibration of the waveguide can cause the supporting inner tube heat ingress seriously, and ultrasonic transmission efficiency can become extremely low, and ultimately lead to system instability.

Formulas (1) and (2) ensure the minimization of this lateral vibration by constraining the upper and lower side cutting lengths, curvature radians, thickness and angle of the blade, while keeping this small lateral vibration only in the area of the blade and the waveguide remains pure longitudinal vibration. The diameter relationship between the thinner and body section of the waveguide is constrained to reduce the instability of the system by reducing the other potential resonant frequencies that otherwise may be excited.

As a blade with one-sided cutting to increase the operating precision of the blade, the present invention presents an arc-shaped groove cutting feature to reduce the left-right lateral vibration of the blade and to ensure the pure longitudinal vibration of the waveguide. The diameter relationship between the thinner and body section of the waveguide is constrained to reduce the instability of the system by reducing the other potential resonant frequencies that otherwise may be excited.

DETAILED DESCRIPTION

In order to enable the technical personnel in the art to better understand the technical scheme of the present invention, the following combined with the specific embodiments of the present invention provides further detailed explanation.

Figure 1:
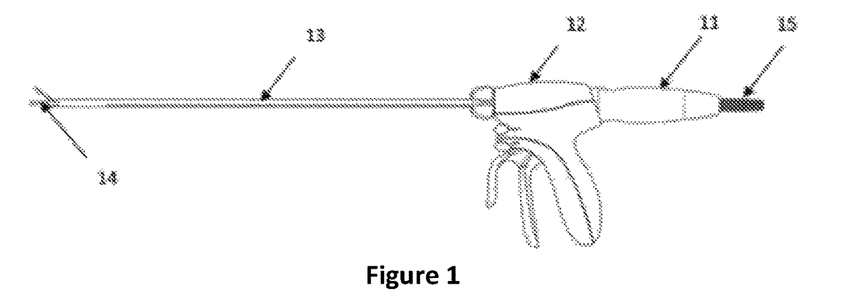
FIG. 1 is an embodiment of the present invention for the hand piece and instrument used for laparoscopic or open surgeries.
Figure 2:
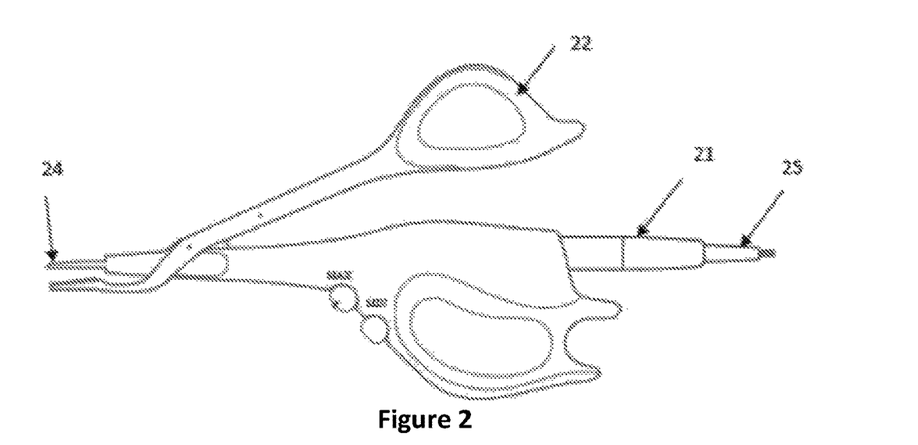
FIG. 2 is an embodiment of the present invention for the hand piece and instrument used for open surgeries.

Ultrasonic scalpel system usually consists of three main parts: ultrasonic generator, hand piece and instrument. Here the connected hand piece and instrument are referred to as a hand-held device. Depending on the ease of operation, there are two types of hand-held devices as shown in FIGS. 1 and 2 that are more suitable for the laparoscopic surgery and open surgery, respectively. Ultrasonic generator provides an ultrasonic frequency electric signal, through the connection of cables 15 and 25 to drive the hand pieces 11 and 21 to vibrate; through the waveguides inside the instruments, the hand piece ultrasonic vibration is transmitted to the blades 14 and 24; the contacting between the blade and tissue produces cutting and coagulating effects.

The gain of the hand-held device is determined by the hand piece and the instrument. For the instrument, the waveguide is the key ultrasonic functional part, thus the gain of the waveguide (including the distal end blade) contributes to the system gain. In order to achieve different technical effects, such as length, gain, vibration mode, reduced thermal damage, improved coagulation and precise control, in order to facilitate understanding, combined with the included Figures, the present invention details the following technical features of the waveguide design.

Figure 7:
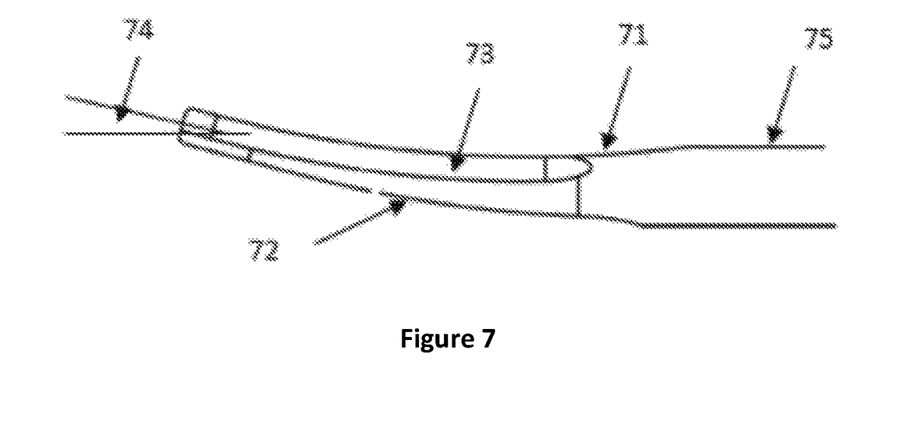
FIG. 7 is a zoom-in view of the blade shown in the embodiment of the present invention, FIG. 3-FIG. 6.
Figure 8:
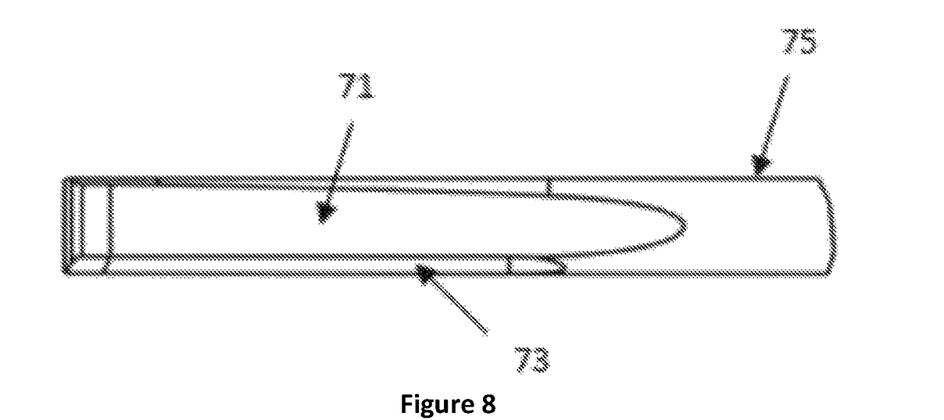
FIG. 8 is the top view of FIG. 7 provided by the embodiment of the present invention.
Figure 9:
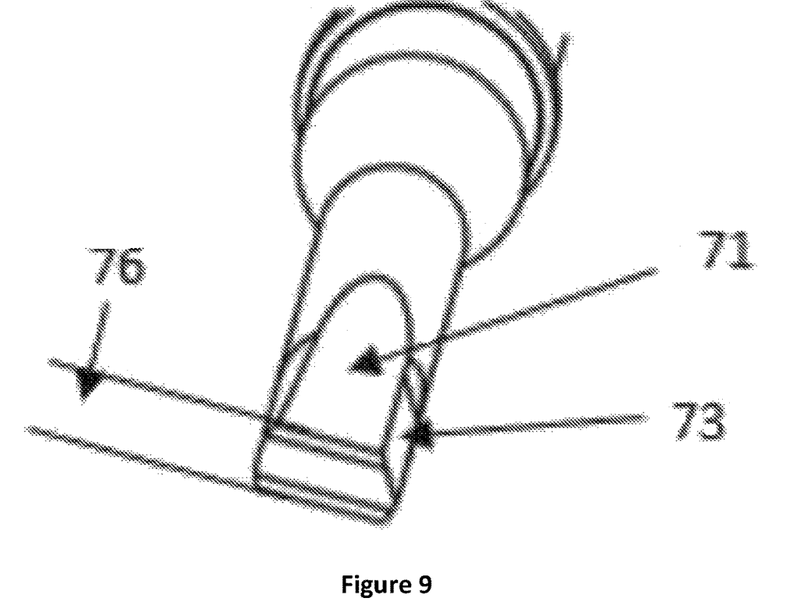
FIG. 9 is the end view of FIG. 7 provided by the embodiment of the present invention.

FIG. 7 shows a blade design, FIG. 8 is the top view of FIG. 7, and FIG. 9 is the end view of FIG. 7. The blade that is gradually slender towards the front is conducive to precise cutting, and the curved shape facilitates the doctor's operation and field of view. But for such a blade, the blade itself will produce a lateral vibration in the direction of bending. If without a well-balanced design, such a lateral vibration will cause the lateral vibration of the waveguide, resulting in the entire waveguide does not have a valid node to secure the outside housing tube, and even cause the vibration of the hand piece shell. All of these should be avoided in the design of an ultrasonic scalpel system. At the same time, if the lateral vibration of the blade in the bending direction is too large, it may increase the thermal damage to the surrounding tissues. This invention proposes the following design scheme to reduce the aforementioned lateral vibration and to minimize the resulting thermal damage.

The blade bends on both sides with cutting face 71 concave and 72 convex and includes side surfaces 73. Concave cutting face 71 length is L1, radius is R1; convex cutting face 72 length is L2, radius is R2; the angle 74 of the center line bending is a; the proximal end 75 of the blade diameter is D; the thickness 76 of the distal end of the blade is T. The relationship among them is:

$$L1 = L2 + L2/1.5*(D-T)*\mathrm{SIN}(\alpha)$$

$$R1 = R2 + 2*T$$

The range of each size can be adjusted within 10%.

Preferably, the radius R1 of the upper side cutting concave surface 71 is 32-36 mm, more preferably 34 mm; Preferably, the radius R2 of the lower side cutting convex surface 72 is 34-38 mm, more preferably 36 mm.

The blade designed according to the above scheme greatly reduces the lateral vibration of the blade itself and of the waveguide, but for the different lengths of the waveguide, a consistent and appropriate gain is required. This invention proposes the following scheme to control the gain of the waveguide in which the above blade is applied.

FIG. 3-FIG. 6 illustrate the different lengths of the waveguide that used the above described blade.

Figure 6:
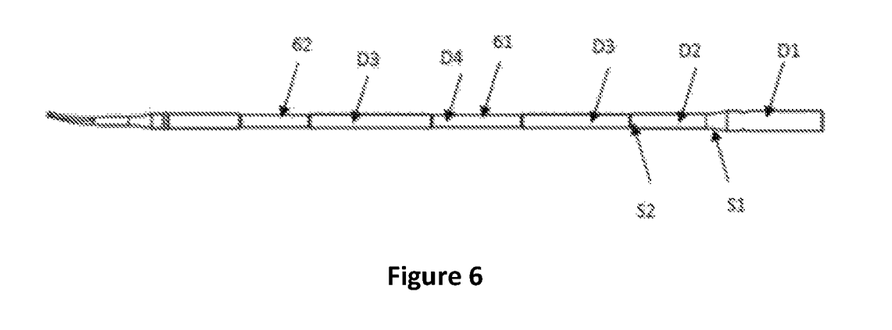
FIG. 6 is an embodiment of the present invention for a waveguide used for an instrument about 13 cm in length.

The proximal section of the waveguide has two steps S1 and S2, indicating in FIG. 6. The proximal end diameter is D1, the second proximal diameter distal to the first step S1 is D2; the third proximal diameter distal to the second step S2 is D3. The ratios among them are:

$$D3:D2:D1 = (0.679 \sim 0.721):(0.7519 \sim 0.7081): (0.97 \sim 1.03)$$

Preferably, D1 is 4.5-5.5 mm, more preferably, 4.7 mm.

Figure 3:
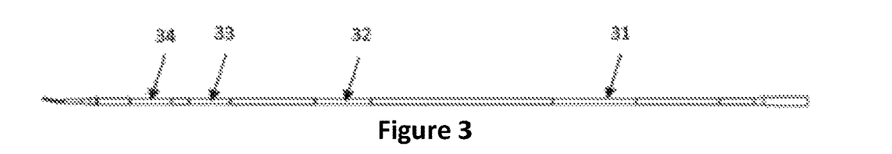
FIG. 3 is an embodiment of the present invention for a waveguide used for an instrument about 35 cm in length.
Figure 4:
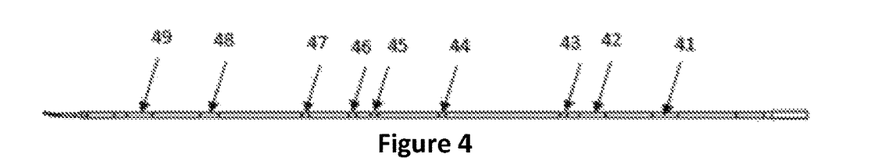
FIG. 4 is an embodiment of the present invention for a waveguide used for an instrument about 45 cm in length.

For waveguides of different lengths, it is sometimes necessary to add a number of cut sections such as 31-34, 41-49, and 61-62 on the body of the waveguide to eliminate other potential resonant frequencies. This invention proposes the following scheme to add such cutting sections.

For the cutting sections, such as 61 and 62, etc., diameter is D4, the diameter of the area between the cutting sections is the same as the third proximal diameter distal to the second step S2, which is D3, the ratio between them is:

$$D4:D3=(0.8827\sim 0.9373):(0.97\sim 1.03)$$

FIG. 3 is a waveguide used for 35 cm long instrument, preferably, cut four thinner sections on the body; preferably, the total length is 399-405 mm, more preferably 402 mm; The four thinner sections are 31, 32, 33 and 34; preferably, the distance between the proximal section 31 and the proximal end is 88-94 mm, more preferably 80 mm; preferably, the length of the section 31 is 40-48 mm, more preferably 44 mm. Preferably, the distance of the most distal section 34 from the distal end of the wave guide is 42-50 mm, more preferably 46 mm; preferably, the length of the section 34 is 18-26 mm, more preferably 22 mm.

FIG. 4 is a waveguide used for 45 mm long instrument, preferably, the total length of the waveguide is 491-497 mm, more preferably 494 mm; preferably, cut nine thinner sections 41-49; preferably, the distance between the proximal section 41 and the proximal end is 79-87 mm, more preferably 83 mm; preferably, the length of the section 41 is 13-21 mm, more preferably 17 mm. Preferably, the distance of the most distal section 49 from the distal end of the wave guide is 50-58 mm, more preferably 54 mm; preferably, the length of the section 49 is 13-21 mm, more preferably 17 mm.

Figure 5:
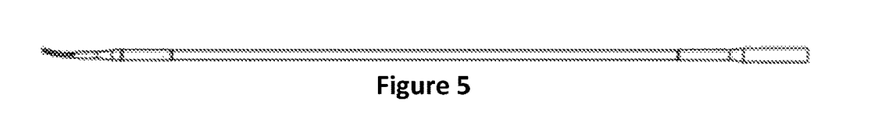
FIG. 5 is an embodiment of the present invention for a waveguide used for an instrument about 22 cm in length.

FIG. 5 is a waveguide used for 22 mm long instrument; the total length is 271-277 mm, preferably 274 mm. For the waveguide of this length, there is no need to add the thinner sections.

FIG. 6 is a waveguide used for 13 mm long instrument; the total length of the waveguide is 183-189 mm, preferably 186 mm; cut two thinner sections 61 and 62; the distance between the proximal section 61 and the proximal end is 68-76 mm, preferably 72 mm; the length of the section 61 is 18-26 mm, preferably 22 mm. The distance of the distal section 62 from the distal end of the waveguide is 42-50 mm, preferably 46 mm; the length of the section 62 is 13-21 mm, preferably 17 mm.

In order to improve the operating precision of the blade, it is necessary to reduce the distal end size of the blade to make it smaller. At present, the commonly used ultrasonic blade is in one-dimensional direction, such as bending direction, small size; while the other direction is flat, the size is still large. The following solutions are proposed to solve this problem.

Figure 10:
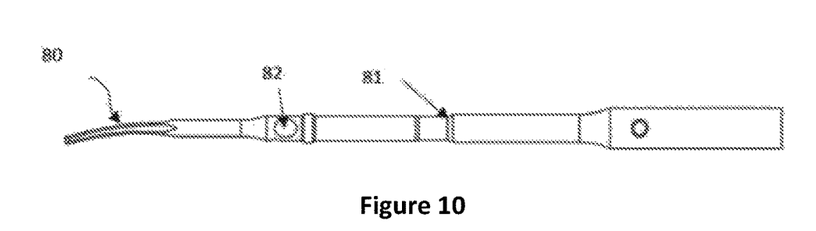
FIG. 10 is an embodiment of the present invention for a waveguide used for an instrument with a length of about 9 cm.
Figure 11:
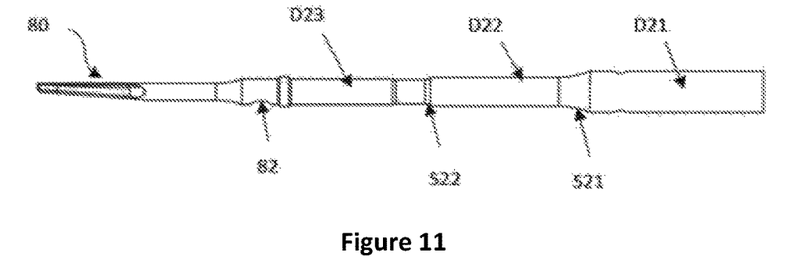
FIG. 11 is the top view of FIG. 10 of the embodiment of the present invention.
Figure 12:
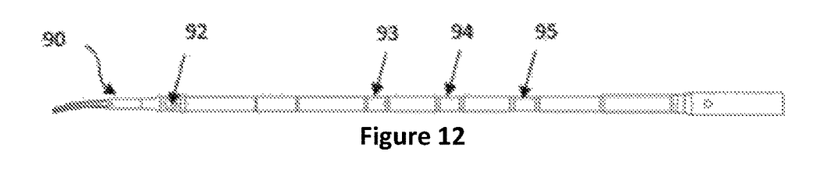
FIG. 12 is an embodiment of the present invention for a waveguide used for an instrument with a length of about 17 cm.
Figure 13:
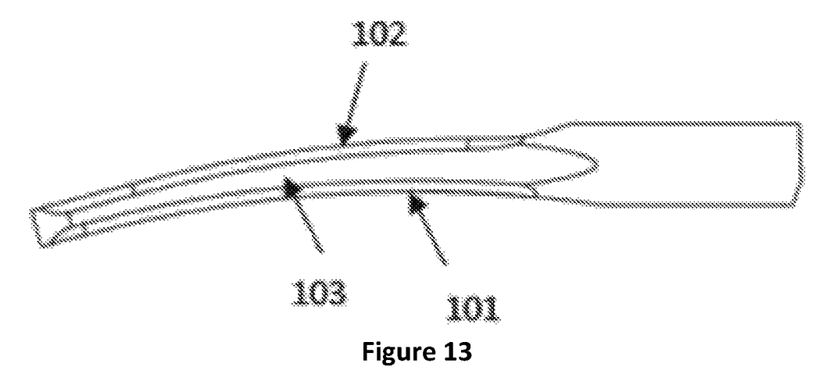
FIG. 13 is a zoom-in view of the blade shown in the embodiment of the present invention, FIG. 10 and FIG. 12.
Figure 14:
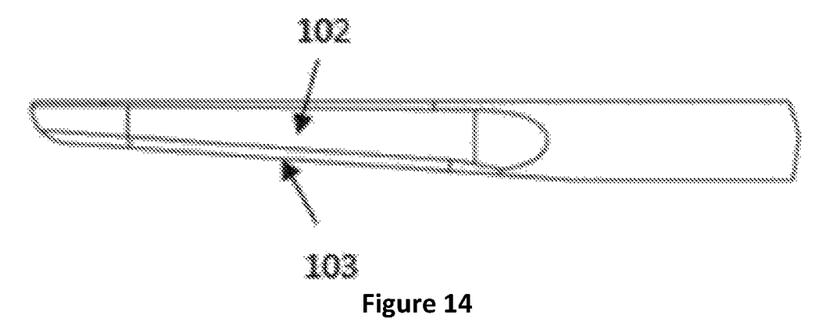
FIG. 14 is the top view of FIG. 13 of the embodiment of the present invention.
Figure 15:
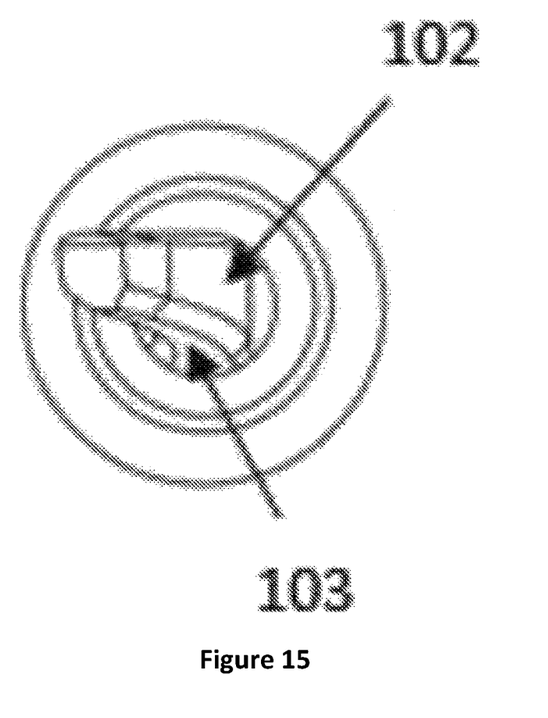
FIG. 15 is the left view of FIG. 14 of the embodiment of the present invention.

FIGS. 13-15 show the diagram of this type of blade. FIG. 14 is the top view of FIG. 13, and FIG. 15 is the left view of FIG. 14. FIG. 13 is also a zoom-in view of the blade shown in FIG. 10 and FIG. 12. FIG. 11 is the top view of FIG. 10. The blade can be curved or be straight. The upper and lower side surfaces have each cutting surfaces. Relative to the upper and lower side surfaces, the left side of the blade or the right side has a gradually narrowed cutting surface 103 toward the distal end of the blade; only one side face has the cutting surface, the other side face has not, as shown in FIG. 14. In order to balance this asymmetric cutting on the blade that may cause lateral vibration of the waveguide as shown in FIGS. 10 and 12, an arc-shaped groove 82 and 92 are added. This groove is within ¼ wavelength (corresponding to the operating frequency of the waveguide) from the distal end, and on the same side with the gradual narrowed cutting 103.

Preferably, the distance of the groove center to the blade distal end is 27-33 mm, more preferably 30 mm; the groove radius is 2-3 mm, more preferably 2.5 mm; the groove depth is 0.2-0.8 mm, more preferably 0.5 mm.

Preferably, the gradual narrowed cutting length is 12-18 mm, more preferably 15 mm; the blade distal end cut is 0.8-1.4 mm, more preferably 1.1 mm. Preferably, the blade is curved, and the cuttings on the upper and lower sides are not symmetric with the waveguide center axis. Concave 101 on the lower side has radius 32-36 mm, preferably 34 mm, and length 13-17 mm, preferably 15 mm. Convex 102 on the upper side has radius 34-38 mm, preferably 36 mm, and length 10-14 mm, preferably 12 mm. Concave 101 has longer length than convex 102 has, and concave 101 has smaller radius than convex 102 has.

The blade designed according to the above scheme greatly reduces the lateral vibration of the blade itself and of the waveguide, but for the different lengths of the rod, a consistent and appropriate gain is required. This invention proposes the following scheme to control the gain of the waveguide that used the above described blade.

FIGS. 10 and 12 illustrate different lengths of the waveguide that used the above described blade.

As shown in FIG. 11, there are two steps S21 and S22 on the proximal portion of the waveguide. The proximal diameter is D21, the second proximal diameter distal to the step S21 is D22, and the third proximal diameter distal to the second step S22 is D23. The ratios among them are:

$$D23:D22:D21=(0.6014\sim 0.6386):(0.7004\sim 0.6596):(0.97\sim 1.03)$$

Preferably, D21 is 5-6 mm; more preferably 5.5 mm.

For waveguides of different lengths, it is sometimes necessary to add several cutting sections to the body to eliminate other potential resonant frequencies.

FIG. 10 is the waveguide used for 9 cm long instrument, preferably, the total length of the waveguide is 93-99 mm, preferably 96 mm. There is a step 81 on the waveguide; it is 41 to 49 mm from the waveguide proximal end, preferably 45 mm.

FIG. 12 is the waveguide used for 17 mm long instrument, preferably, the total length of the waveguide is 180-186 mm, preferably 183 mm. There are three cutting sections 93-95 on the waveguide; the proximal section 95 is 57-65 mm from the proximal end, preferably 61 mm; the length of the section 95 is 3-11 mm, preferably 7 mm. The third section 93 is 95-103 mm from the proximal end, preferably 99 mm; the length of the section 93 is 2-10 mm, preferably 6 mm.

The above is only the preferred embodiment of the present invention. It should be pointed out that the above-mentioned preferred embodiment shall not be regarded as a limitation of the present invention. The scope of protection of the present invention should be subject to the scope of the claims. For ordinary skill in the art, within the spirit and scope of the present invention, can also make a number of improvements and modifications; these improvements and modifications should also be regarded as within the protection scope of the present invention.

The invention claimed is:

1. An ultrasonic surgical blade, comprising:
    opposing sides and a thickness, wherein the ultrasonic surgical blade is curved, and wherein the opposing sides of the ultrasonic surgical blade are provided with first and second cutting surfaces, wherein the first cutting surface is delimited by opposing first edges and is concave, and wherein the second cutting surface is delimited by opposing second edges and is convex, wherein the first edges of the first cutting surface and the second edges of the second cutting surface are separated from each other by first and second side surfaces, wherein the first and second side surfaces are delimited by opposing pairs of the first and second edges, the thickness of the ultrasonic surgical blade gradually thinning along a cutting direction from a proximal end to a distal end, wherein a concave length of the first cutting surface is L1, a convex length of the second cutting surface is L2, a concave curvature radius of the first cutting surface is R1, and a convex curvature radius of the second cutting surface is R2, and wherein equations (1) and (2) are:

$$L1 = L2 + \frac{L2}{1.5} \times (D - T) \times \sin\alpha \quad (1)$$

$$R1 = R2 + 2T \quad (2)$$

where $\alpha$ is a bent angle of a blade center line, D is a proximal end diameter of the ultrasonic surgical blade, and T is the thickness of the ultrasonic surgical blade distal end, and wherein the values of L1 and R1 are calculated by formulas (1) and (2), and a range of each value is ±10%.

2. An ultrasonic surgical waveguide, comprising the ultrasonic surgical blade as described in claim 1, wherein a proximate portion of the ultrasonic surgical waveguide has first and second proximal steps, wherein the proximal end diameter D is D1, a second proximate diameter distal to the first proximal step is D2, a third proximate diameter distal to the second proximal step is D3, and a ratio among D3, D2, and D1 is:

D3:D2:D1=(0.679~0.721):(0.7519~0.7081):
(0.97~1.03).

3. An ultrasonic surgical waveguide comprising:
an ultrasonic surgical blade comprising opposing sides and a thickness, wherein the ultrasonic surgical blade is curved, and wherein the opposing sides of the ultrasonic surgical blade are provided with first and second cutting surfaces, wherein the first cutting surface is concave and the second cutting surface is convex, the thickness of the ultrasonic surgical blade gradually thinning along a cutting direction from a proximal end to a distal end, wherein a concave length is L1, a convex length is L2, a concave curvature radius is R1, and a convex curvature radius is R2, and wherein equations (1) and (2) are:

$$L1 = L2 + \frac{L2}{1.5} \times (D - T) \times \sin\alpha \quad (1)$$

$$R1 = R2 + 2T \quad (2)$$

where $\alpha$ is a bent angle of a blade center line, D is a proximal end diameter of the ultrasonic surgical blade, and T is the thickness of the ultrasonic surgical blade distal end, and wherein the values of L1 and R1 are calculated by formulas (1) and (2), and a range of each value is ±10%, wherein a proximate portion of the ultrasonic surgical waveguide has first and second proximal steps, wherein the proximate end diameter D is D1, a second proximate diameter distal to the first proximal step is D2, a third proximate diameter distal to the second proximal step is D3, and a ratio among D3, D2, and D1 is:

D3:D2:D1=(0.679~0.721):(0.7519~0.7081):
(0.97~1.03), wherein the ultrasonic surgical waveguide has a plurality of sections having a diameter D4 that is smaller than D1, D2, and D3 wherein a diameter of an area between the plurality of sections is the same as the third proximate diameter D3, and wherein a ratio between D4 and D3 is:

D4:D3=(0.8827~0.9373):(0.97~1.03).

4. An ultrasonic scalpel, comprising:
a hand piece, and
the ultrasonic surgical waveguide according to claim 2.

5. An ultrasonic surgical blade, comprising:
first and second cutting surfaces on both upper and lower sides, respectively, of the ultrasonic surgical blade, wherein the first cutting surface is concave and delimited by opposing first edges, wherein the second cutting surface is convex and delimited by opposing second edges, wherein the first edges of the first cutting surface and the second edges of the second cutting surface are separated from each other by first and second side surfaces, wherein the first and second side surfaces are delimited by opposing pairs of the first and second edges;

relative to the upper and lower sides, only one side surface of the ultrasonic surgical blade has a gradually smaller cutting surface toward a distal end of the ultrasonic surgical blade;

wherein a proximate end of the ultrasonic surgical blade has an arc-shaped groove; and wherein the arc-shaped groove is within ¼ wavelength from the distal end, and is located at a same side surface as the gradually smaller cutting surface.

6. An ultrasonic surgical waveguide, comprising:
the ultrasonic surgical blade as described in claim 5,
a proximate portion of the ultrasonic surgical waveguide having first and second proximal steps, and
a proximate end diameter is D21, a second proximate diameter distal to the first proximal step is D22, a third proximate diameter distal to the second proximal step is D23, and wherein a ratio among D21, D22, and D23 is:

D23:D22:D21=(0.6014~0.6386):(0.7004~0.6596):
(0.97~1.03).

7. An ultrasonic scalpel, comprising:
a hand piece and the ultrasonic surgical waveguide of claim 6, wherein the hand piece, the ultrasonic surgical waveguide, and the ultrasonic surgical blade are connected in sequence.

8. A method of using the ultrasonic scalpel according to claim 7, wherein the method comprises cutting using the ultrasonic surgical blade.

* * * * *

UNITED STATES PATENT AND TRADEMARK OFFICE
CERTIFICATE OF CORRECTION

| | | |
|---|---|---|
| PATENT NO. | : 11,571,235 B2 | Page 1 of 1 |
| APPLICATION NO. | : 16/649495 | |
| DATED | : February 7, 2023 | |
| INVENTOR(S) | : Zhongyu Yan et al. | |

It is certified that error appears in the above-identified patent and that said Letters Patent is hereby corrected as shown below:

In the Claims

<u>Column 8, Claim 3, Line 6:</u>
"the proximate end" should read: --the proximal end--.

Signed and Sealed this
Fourth Day of February, 2025

Coke Morgan Stewart
*Acting Director of the United States Patent and Trademark Office*